United States Patent [19]

Ganguly et al.

[11] Patent Number: 4,767,748
[45] Date of Patent: * Jul. 30, 1988

[54] SUBSTITUTED OLIGOSACCHARIDE ANTIBODIES

[75] Inventors: Ashit K. Ganguly, Upper Montclair; Olga Sarre, Verona; Viyyoor M. Girijavallabhan, Parsippany, all of N.J.

[73] Assignee: Schering Corporation, Kenilworth, N.J.

[*] Notice: The portion of the term of this patent subsequent to Nov. 11, 2003 has been disclaimed.

[21] Appl. No.: 900,873

[22] Filed: Aug. 27, 1986

Related U.S. Application Data

[63] Continuation-in-part of Ser. No. 787,405, Oct. 15, 1985, Pat. No. 4,622,314.

[51] Int. Cl.[4] .................. C07H 15/24; C07H 15/00; A61K 21/00; A61K 35/74
[52] U.S. Cl. .................... 514/54; 536/16.8; 536/17.9; 536/18.1; 514/25
[58] Field of Search ............ 536/16.8, 17.9, 18.1, 536/123; 514/54, 25; 424/116

[56] References Cited

U.S. PATENT DOCUMENTS 4,264,591  4/1981  Bauer et al. .................. 536/18.1
4,597,968  7/1986  Waitz et al. .................. 424/115

FOREIGN PATENT DOCUMENTS 2361582  6/1974  Fed. Rep. of Germany ..... 536/16.8
2805408  8/1978  Fed. Rep. of Germany ..... 536/16.8

OTHER PUBLICATIONS

Sattler, A. et al. "The Everninomicins, Biosynthetic Studies" J. of Antibiotics 23(4):210–215 (1970).

*Primary Examiner*—Ronald W. Griffin
*Assistant Examiner*—Nancy S. Carson
*Attorney, Agent, or Firm*—Thomas D. Hoffman; Gerald S. Rosen

[57] ABSTRACT

A compound represented by formula I

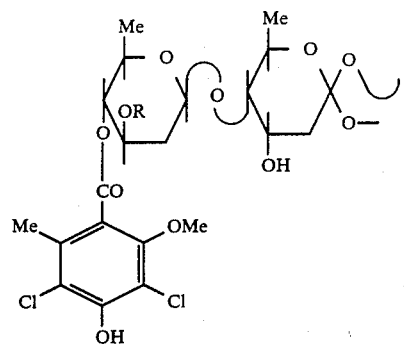
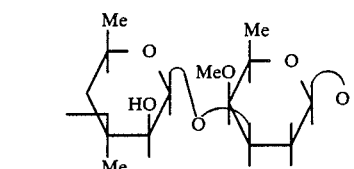
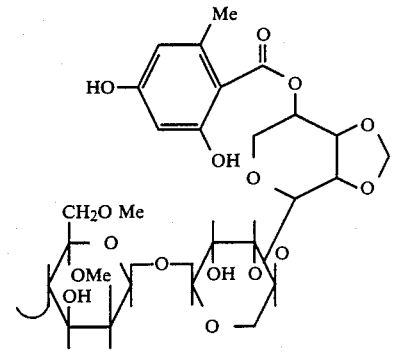

wherein R is hydrogen, or

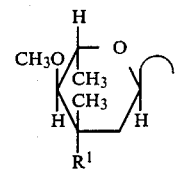

wherein $R^1$ is N-acylamino, N-alkylamino, N,N-dialkylamino, N-acyl-N-hydroxylamino, nitroso or the pharmaceutically acceptable salts thereof.

11 Claims, No Drawings

4,767,748

SUBSTITUTED OLIGOSACCHARIDE ANTIBODIES

CROSS-REFERENCE TO RELATED APPLICATION

This application is a Continuation-In-Part Application of U.S. patent application, Ser. No. 787,405 filed Oct. 15, 1985 now U.S. Pat. No. 4,122,314.

BACKGROUND OF THE INVENTION

This invention relates to anti-bacterially active derivatives of an antibiotic complex produced by *Micromonospora carbonacea var africana var nov.* NRRL 15099, ATCC 39149, which is designated antibiotic 13-384 in commonly assigned U.S. Pat. No. 4,597,968 which is incorporated herein by reference. This complex, the method of producing and isolating it, its components 1 and 5 and their use as antibacterial agents are disclosed, in said U.S. Patent. More specifically, this invention relates to derivatives of the components of the complex designated components 1 and 5 of antibiotic 13-384 and their antibacterial compositions, as well as methods of treating antibacterial infections therewith.

SUMMARY OF THE INVENTION

The present invention is directed to the desevernitrose, N-acylamino, e.g., acetamido, N-alkylamino, e.g., ethylamino, N,N-dialkylamino, e.g., diethylamino and N-acyl-N-hydroxylamino derivatives of antibiotic 13-384 components 1 and 5, represented by the following formula I:

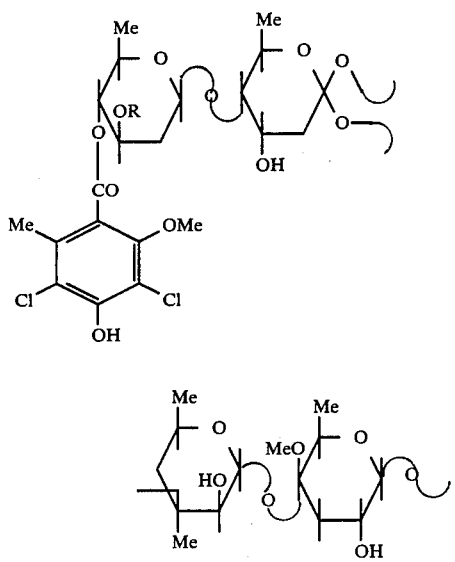

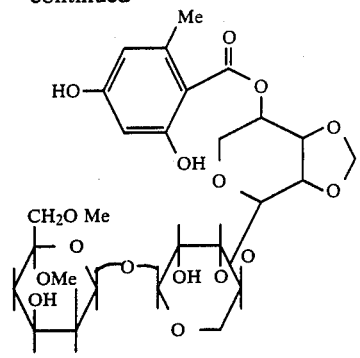

wherein R is hydrogen, or

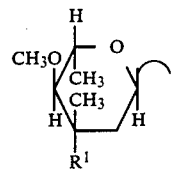

wherein $R^1$ is N-acylamino, N-alkylamino, N,N-dialkylamino, N-acyl-N-hydroxylamino, or a pharmaceutically acceptable salt thereof.

The compounds of formula I have three phenolic moities which are acidic and as such react with alkali or alkaline earth bases or ammonia or substituted amines to form pharmaceutically acceptable salts. Typical suitable pharmaceutically acceptable salts of the compounds of formula I are the alkali or alkaline earth metal salts or the ammonium or substituted ammonium salts. Typical suitable substituted ammonium salts are those derived from organic amines such as trialkylamines, especially tri-alkyl amines, procaine, dibenzylamine, N-benzylbetaphenethylamine, N,N'-dibenzylalkylenediamine, dehydroabiethylamine, N,N'-bisdehydroabiethylethylenediamine, N-alkylpiperdines, e.g., N-ethylpiperidine and N-methylglucamine. The preferred substituted ammonium salt is the one derived from N-methylglucamine. Representative alkali metal and alkaline earth metal salts are derived from the hydroxides and include the sodium, potassium, and calcium salts; preferred are sodium salts. While the preferred pharmaceutically acceptable salts are of the catonic type, acid addition salts may also be used.

The compounds of this invention possess antibacterial activity against both gram-positive and gram-negative bacteria. Generally, the compounds of this invention show advantageous activity against methicillin resistant *Staphlococcus aureus.*

Anti-bacterial in vitro activity was also observed against various species of Streptococcus with Minimum Inhibitory Concentrations (MIC's) ranging frcm 0.006 mcg/ml to 16.0 mcg/ml.

Most importantly, the compounds of this invention are injectable antibacterial agents which afford good blood levels at antibacterial dosages.

The present invention also includes within its scope pharmaceutical compositions comprising an anti-bacterially effective amount of a compound of formula I together with a compatible pharmaceutically acceptable carrier. The compounds of formula I may be the only antibacterial agent in the pharmaceutical dosage forms, or may be admixed with other compatible antibacterial agents.

Also contemplated by this invention is the method of effectively treating a warm-blooded animal having a susceptible bacterial infection which comprises administering to said animal an anti-bacterially effective amount of a compound of formula I.

DESCRIPTION OF THE INVENTION

The term "acyl" as used herein means straight and branched chain substituted and unsubstituted alkanoyl groups having 1 to 12 carbons, said substituents being one or more of amino, halo, hydroxy, aryl and thio; cyclized alkanoyl groups having 4 to 12 carbons; aroyl; and alkylaroyl.

Typical suitable straight and branched chain unsubstituted alkanoyl groups include formyl, acetyl propanoyl, n- and iso-butyroyl, valeroyl, pivaloyl, heptanoyl, octanoyl, nonanoyl, and dodecanoyl.

Typical suitable substituted alkanoyl groups include 2-aminoalkanoyl, i.e., those derived from the naturally occurring α-amino acids such as cystine glutamic acid, histidine, hydroxylproline, methionine proline, tyrosine or threonine as well as corresponding D-α-amino acids such as D-ornithine, D-methionine, D-lysine and D-alanine; hydroxyalkanoyl such as those derived from α-hydroxy acids such as glycolic, lactic, mandelic (phenylglycollic), α-hydroxybutyric, α-hydroxyisobutyric, α-hydroxy-n-and-iso-valeric acids as well as α-hydroxy acids such as malic (hydroxysuccinic) and tartaric (dihydroxysuccinic acid); haloalkanoyl, especially α-haloalkanoyl such as chloroacetyl, bromoacetyl, trifluoroacetyl and 2,2-difluoropropanoyl; thio-substituted alkanoyl such as thiolactic and thioglycollic; arylalkanoyl such as phenylacetyl, γ-phenylbutyryl, phenylglycyl, and phenylalanyl.

Typical suitable cyclized alkanoyl groups include cyclopropylcarbonyl, cyclobutylcarbonyl, cyclopentylcarbonyl, cyclohexylcarbonyl, cycloheptylcarbonyl, adamantylcarbonyl, as well as those derived from heterocyclic carboxylic acids such as thiopheneacetic acid, furoic acid (furan-2-carboxylic acid), furanacetic acid and tetrazylacetic acid.

Typical suitable aroyl groups include benzoyl and benzoyl substituted by one or more of halo, nitro, trifluoromethyl and phenyl such as 3-chlorobenzoyl, 4-trifluoromethylbenzoyl, 4-nitro-3-trifluoromethylbenzoyl and 4-phenylbenzoyl.

Typical suitable alkylaroyl include 2-methylbenzoyl, 3-methylbenzoyl and 2,4,6-trimethylbenzoyl.

The term "alkyl" as used herein means straight, branched-chain and cyclized hydrocarbon groups of up to 6 carbons including methyl, ethyl, n-and isopropyl, cyclopropyl, n-, iso-, tert-butyl, cyclobutyl, n-, iso- sec- and tert-pentyl, cyclopentyl, n-, iso-, sec- and tert-hexyl, and cyclohexyl.

Preparation of N,N-Dialkylamino Compounds

Compounds represented by formula I wherein $R_1$ is N,N-dialkylamino may be prepared by reductive alkylation procedures generally known in the art. In an especially suitable process, the compounds of formula I wherein $R_1$ are amino is reacted with excess aldehyde in an inert organic solvent under hydrogen atmosphere (at or slightly above atmospheric pressure) in the presence of a hydrogenation catalyst, especially platinum oxide.

The N,N diethylamino derivative of antibiotic 13-384, component 5 may be prepared by the reduction of the component and acetaldehyde in an inert organic solvent, e.g. 2-methoxyethanol, dimethoxyethane, 2-methoxyethylether or a $C_1$–$C_6$ alkanol, preferably 2-methoxyethanol. The reduction is conducted under pressure in an atmosphere of hydrogen, in the presence of an alkali metal carbonate or bicarbonate, preferably sodium bicarbonate, and platinum oxide as a reducing catalyst, until the reaction is complete, usually about 24 to 48 hours. The pressure used is about 20–30 psi, preferably 25 psi. The product is then recovered using chromatography.

Preparation of N-alkylamino Compounds

Compounds represented by formula I wherein $R_1$ is N-alkylamino may be prepared by reductive alkylation procedures generally known in the art using an active nickel hydrogenation catalyst instead of platinum oxide. In a facile manner, the compounds of formula I wherein $R_1$ is amino may be reacted with an aldehyde in a suitable solvent, such as an alcohol, e.g. 2-methoxyethanol and the reaction mixture is subjected to hydrogenation in the presence of an active nickel catalyst such as active Raney nickel under pressure. Alternatively, N-alkylamino compounds of the present invention may be prepared by reductive alkylation of the Schiffs bases in situ. In this procedure the amino compound may be reacted with the appropriate aldehyde in a suitable alcohol solvent. The reaction product is then reacted with a suitable reducing agent, e.g. sodium cyanoborohydride without isolation. This reaction often yields the desired N-alkylamino compounds in the form of the boron complex which may be treated with aluminum amalgam in aqueous alcohol to yield the desired N-alkylamino compound.

The N-ethyl derivative may be prepared by reaction of the amino compound with acetaldehyde in methanol as a solvent and hydrogen in the presence of a Raney nickel catalyst.

Preparation of Desevernitrose Compound

The desevernitrose derivative of antibiotic 13-384, component 1, may be prepared by the following sequence of reactions, (a) reduction of 13-384 component 1 to the hydroxylamino derivative (b) oxidation of the hydroxylamino 13-384 to the nitroso derivative (c) reaction of the nitroso compound with phosphites or phosphines. The reduction of 13-384 component 1 is carried out in an inert organic solvent e.g. tetrahydrofuran (THF), dioxane, dimethoxyethane or 2-methoxyethylether in the presence of a catalyst e.g. sodium amalgam, zinc-copper complex or zinc powder with a proton source e.g. ammonium chloride, tartaric acid or ammonium carbonate. The reaction is conducted under an inert atmosphere, e.g. nitrogen at room temperature for a time sufficient to produce the N-hydroxylamino derivative, e.g. about 24 to 48 hours. The product is then recovered.

The N-hydroxylamino derivative is then reacted with activated carbon in an inert organic solvent, e.g. methanol, ethanol or other lower alkanols for a time sufficient to complete the reaction, about 5 to 10 hours, to give the nitroso derivative. The product is separated from the activated carbon and recovered.

The nitroso product is reacted under an inert atmosphere e.g. nitrogen with an alkoxy phosphorous compound e.g. triethyl phosphite, tributylphosphite, or arylphosphines e.g. triphenyl phosphine in an inert organic solvent e.g. tetrahydrofuran, dioxane, dimethoxyethane, or 2-methoxyethyl ether. The solution is heated until the reaction is complete. The residue is recovered to give the desevernitrose derivative of antibiotic 13-384, component 1.

Preparation of N-Acyl-N-Hydroxylamino Compounds

The N-acyl-N-hydroxylamino compounds of the present invention may be prepared by reducing 13-384 component 1 in the presence of an acid anhydride using an active zinc metal powder as catalyst.

Normally, four to six times the stoichiometric amount of an acid anhydride of the acyl groups (described hereinabove required to prepare the title compounds) is used. The active zinc catalyst is conveniently prepared by washing zinc metal powder with aqueous mineral acid followed by removal of the water by conventional methods. The reduction of 13-384 component 1 is carried out in an anhydrous inert organic solvent typically anhydrous THF or dioxane under an inert atmosphere at room temperature for a time sufficient to produce a crude reaction mixture of N-acyl-N-hydroxyamino and N-acylamino products. The crude reaction mixture is treated with methanolic ammonia to hydrolyze the acylphenolic esters as well as to destroy the excess acid anhydride. The N-acyl-N-hydroxylamino compounds are then recovered and purified by conventional techniques e.g. extraction and column chromatography.

Preparation of N-Acylamino Compounds

Compounds represented by formula I wherein $R_1$ is amino react with acylating agents, in the absence of base, to yield di-, tri- and tetra-acyl derivatives wherein the amino moiety and one, two or three of the phenolic hydroxyl moieties are acylated. Partial hydrolysis under mild basic conditions readily removes the acyl function from the phenolic hydroxyl moieties thereby yielding the corresponding N-acylamino compounds of the present invention.

Among the acylating agents suitable for acylation are acid anhydrides and mixed acid anhydrides of the acyl groups described hereinabove. Typical suitable mixed acid anhydrides include acid anhydrides formed by reaction of the carboxylic acids of the acyl groups, described hereinabove, such as cyclohexane carboxylic and/or a suitably protected phenylglycine with a chloroformate or p-toluenesulfonyl chloride in the presence of base.

Alternatively, the N-acylamino compounds of the present invention may be prepared by acylation of the amino moiety in the presence of ($C_1$-$C_6$) alcohols such as isopropyl alcohol, thereby avoiding the acylation of the phenolic hydroxyl moieties.

In general, the N-acylamino compounds of the present invention may be purified by standard techniques e.g. crystallization from a suitable solvent or chromatography.

The acetamido derivative of antibiotic 13-384, component 5 may be prepared by the reaction of the component with acetic anhydride in an ether solvent, e.g. tetrahydrofuran, dioxane, dimethoxyethane or an $C_1$-$C_6$ alcohol solvent, e.g. isopropyl alcohol at room temperature, e.g. about 25° C., for about 3 hours. The progress of the reaction is monitored by thin layer chromatography (TLC). The resulting product, the acetamido derivative of antibiotic 13-384, component 5, is then recovered.

Conversion of component 1 (the nitro sugar) into component 5 (the amino sugar) can be accomplished by reduction of component 1 in the presence of active Raney nickel in a suitably inert organic solvent such as ethyl acetate, tetrahydrofuran, 2-methoxyethanol, or ethanol, at a hydrogen pressure 35 psi for 21 hours.

This conversion can also be accomplished by hydrogenating component 1 in the presence of aluminum-mercury amalgam in ethanol or tetrahydrofuran-ethanol mixture. The corresponding derivatives of components 1 and 5 can be made by using component 5 in place of component 1 as described herein and vice versa.

Preparation of the pharmaceutically acceptable salts of compounds of formula I may be carried out according to conventional procedures for forming salts. Salts can be formed, for example, by treating with metal hydroxide compounds such as sodium hydroxide, calcium or magnesium hydroxide, or with ammonia or a suitable organic amine or N-methylglucamine, wherein at least about a stoichiometric amount of the salt-forming agent is used. Acid addition salts of compounds of formula I are obtained in the usual manner, for example, by treating with an acid or a suitable anion exchange reagent.

The antibiotics of the invention may be combined with any suitable pharmaceutical carrier and administered orally, parenterally or topically in a variety of formulations. For oral administration, the antibiotics of this invention may be compounded in the form of tablets, capsules, elixirs or the like. Tablets and capsules may contain such excipients as starch or lactose; liquid forms may contain coloring or flavoring agents. Topical preparations may be in the form of creams, hydrophobic and hydrophilic ointments, or aqueous, non-aqueous or emulsion-type lotions. Typical carriers for such formulations are water, oils, greases, polyesters and polyols. Parenteral formulations, e.g., injectable dosage forms, are usually liquids such as solutions or suspensions, with typical carriers being distilled water and saline solution.

Typical pharmaceutically carriers for use in the pharmaceutical formulations of the compounds of this invention are exemplified by sugars such as lactose, sucrose, mannitol and sorbitol; starches such as corn starch, tapioca starch and potato starch; cellulose and derivatives such as sodium carboxymethyl cellulose, ethyl cellulose and methyl cellulose; calcium phosphates such as dicalcium phosphate and tri-calcium phosphate; sodium sulfate; calcium sulfate; polyvinyl pyrrolidone; polyvinyl alcohol; stearic acid; alkaline earth metal stearates such as magnesium stearate; vegetable oils such as peanut oil, cottonseed oil, sesame oil, olive oil and corn set; non-ionic, cationic and anonic surfactants, ethylene glycol polymers; betacyclodextrin; fatty acids, hydrolyzed cereal solids; water; polyalkylene glycols; gums; and petroleum; as well as other non-toxic compatible fillers, binders, disintegrants and lubricants commonly used in pharmaceutical formulations. The compositions may also contain preservatives, aerosol propellants and coloring, thickening, suspending, dispensing, emulsifying, wetting, stabilizing and buffering agents.

The dose to be administered in any particular dosage form will depend upon various factors, such as the susceptibility of the infecting organism to the antibiotic, the stage and severity of the infection. Generally, the dosage administered is from about 1.0 mg to about 25 mg per kilogram of body weight per day, in divided dosages, the specified dosage being left to the discretion of the practitioner. In treating certain patients with the compounds of this invention, it is possible to include other pharmaceutically active ingredients in the same dosage unit.

The following examples illustrate the preparations of the compounds of the present invention, wherein the structure of the compounds were verified by Infrared Spectroscopy (IR), Proton Magnetic Resonance PNMR, $C^{13}$ Magnetic Resonance (CNMR), and High Resolution Fast Atom Bombardment Mass Spectrometry, (MS/FAB).

EXAMPLE I

N,N-Diethylamino-13-384-Component 5

A solution of 200 mg of 13-384, component 5, as isolated and purified in U.S. Pat. No. 4,597,968 in 8 ml of 2-methoxyethanol and 2 ml of freshly distilled acetaldehyde was stirred under hydrogen in the presence of 40 mg of sodium bicarbonate and 200 mg of platinum oxide at 25 psi for 48 hours. The catalyst was filtered off and the filtrate concentrated to dryness, under vacuum, to yield crude title compound. Chromatography on a silica gel column, eluting with 5% v/v of methanol in chloroform, yielded pure title compound. Anal: found; C, 50.13; H,6.33; N, 0.74%; $C_{74}H_{107}O_{36}NCl_2 \cdot CHCl_3$ requires C, 50.69; H,6.13; N, 0.79%; MS:(FAB)[m+H]+1656; Rotation: $[\alpha]_D^{26}$ −45.9° (MeOH); CNMR: δ119.357 ppm and δ 120.529 ppm (ortho esters).

The N,N-diethylamino-13-384-component-1 derivative can also be made by reducing component 1 to component 5 and then following the procedure in the above example.

EXAMPLE II

N-Ethylamino-13-384-Component 5

A solution of 150 mg of 13-384, component 5 as isolated and purified in U.S. Pat. No. 4,597,968 in 3 ml of methanol and 3 ml of freshly distilled acetaldehyde was stirred under hydrogen in the presence of 35 mg of sodium bicarbonate and Raney nickel (about 1.5 ml) at 25 psi for 48 hours. The catalyst was filtered off and the solvent was removed under reduced pressure to yield the title compound. Chromatography on a silica gel column, eluting with 10% v/v of methanol in chloroform, yielded pure title compound. Anal.: Found: C, 51,96; H,6.24; H,0.97; $C_{72}H_{103}O_{36}NCl_2 \cdot \frac{1}{2} CHCl_3$ requires: C,51.60; H,6.18; N,0.83%; MS/FAB $(M+H)^+1628$; Rotation: $[\alpha]_D^{26}$ −45.3° (MeOH); CNMR: δ 119.277 ppm and δ 120.488 ppm (ortho esters).

The N-ethylamino-13-384-component 5 derivative can also be made by reducing component 1 to component 5 and then following the above example.

EXAMPLE III

Desevernitrose-13-384-Component 1

(a) N-Hydroxylamino-13-384-Component-1

To a solution of 1.0 g of 13-384 component 1, as isolated and purified in U.S. Pat. No. 4,597,968 in 30 ml of peroxide free tetrahydrofuran (THF) was added 600 mg of zinc powder. To the stirring slurry was added, dropwise, 2 ml of a 10% aqueous solution of ammonium chloride. The suspension was stirred under nitrogen at room temperature for 35 minutes. The progress of the reaction was monitored by TLC using 8% v/v methanol in chloroform as eluent. The filtered reaction mixture was washed twice with brine solution. The organic layer was dried over anhydrous sodium sulfate and concentrated under reduced pressure to yield the title compound.

(b) Nitroso-13-384-Component-1

To a solution of 960 mg of crude hydroxylamino -13-384, component 1, in 30 ml of methanol was added 2 g of "NUCHAR" 12×40 mesh active carbon (Westvaco Chemical Division). The suspension was stirred at room temperature for 7 hours. The progress of the reaction was followed by TLC using 8% v/v methanol in chloroform as eluent. The "NUCHAR" was filtered off on a buchner funnel using a filter pad, and thoroughly washed with methanol. The clear filtrate was concentrated to dryness under reduced pressure. The "NUCHAR" was further extracted with tetrahydrofuran to give crude title compound.

(c) Desevernitrose-13-384-Component-1

Under nitrogen atmosphere, to a solution of 500 mg of crude nitroso-13-384, component 1, in 16 ml of peroxide free dioxane was added 1.6 ml of triethylphosphite. The reaction solution was heated in a 100° C. oil bath, with stirring, until TLC analysis indicated the absence of starting compound (about 2 hours). The reaction mixture was evaporated to a residue under vacuum. The residue was dissolved in a minimal amount of tetrahydrofuran and slowly precipitated with hexane. The precipitate was filtered and thoroughly washed with hexane. The crude title compound was chromatographed through a silica gel column, eluting with 3% v/v of methanol in chloroform, to give pure title compound, which may be further purified by crystallization from acetone. Anal.: found: C,51.45; H,5.97%; $C_{62}H_{84}O_{34}Cl_2$ requires: C,51.56; H,5.86%; M.P. 198°-202° C.; MS/FAB: (M+DEAH)+1548; M+1442; Rotation: $[\alpha]_D^{26}$ −20.7° (MeOH); PNMR and IR were consistent with the assigned structure.

EXAMPLE IV

Acetamido-13-384-Component-5

To a solution of 200 mg of antibiotic 13-384, component 5, in 13 ml of peroxide free tetrahydrofuran was added 85 mg of sodium bicarbonate and 0.1 ml of acetic anhydride. The reaction mixture was stirred at room temperature until TLC analysis, in 18% v/v of methanol in chloroform, indicated the absence of starting compound (about 3 hours). The reaction mixture was filtered and the clear filtrate was concentrated to a residue under reduced pressure. Titration of the residue gave solids of crude multiacetylated 13-384, component 5. The solids were dissolved in 2.5 ml of 5% ammonium hydroxide in methanol and allowed to stand at room temperature for about 40 minutes. The progress of the reaction was monitored by TLC, using 10% v/v of methanol in chloroform. The reaction solution was concentrated to a low volume, under reduced pressure, diluted with ethyl acetate and again concentrated to a lower volume. The residue was then partitioned between ethylacetate and water, and separated. The aqueous portion was extracted with ethylacetate. The combined ethylacetate extracts were washed once with brine, dried over sodium sulfate, and evaporated to a residue, under reduced pressure, to give crude title compound. Chromatography of the crude title compound on four preparative thin layer silica gel plates (1,000 microns thick) using 10% v/v of methanol in chloroform as eluent, and extraction of the product off of the silica gel with distilled tetrahydrofuran gave the title compound. Anal.: found: C,52.14; H,6.25; N,0.69%; $C_{72}H_{101}O_{37}NCl_2$ requires: C,52.62; H,6.19 and N,0.85%; MS/FAB (M+DEAH)+1747; M+1641; $[\alpha]_D^{26}$ −47.3° (MeOH). IR was consistent with the assigned structure.

Acetamido-13-384-Component 5 can also be made from Component 1 by reduction to Component 5 followed by acetylation as in the above example.

EXAMPLE V

N-Cyclohexylcarbonylamino-13-384-Component-5

Dissolve 1.3 g of cyclohexane carboxylic acid and 1.05 g of triethylamine in 20 mL of anhydrous tetrahydrofuran. Cool the reaction mixture to about 5°-10° C. and add 1.1 g of ethyl chloroformate with agitation. Continue agitating the reaction mixture for an additional 10 min. and filter. Add to the clear filtrate 300 mg of antibiotic 13-384 component 5 as isolated and purified in U.S. Pat. No. 4,597,968 and continue agitating the reaction mixture. Monitor the procress of reaction by TLC as described in Example IV. When the reaction is complete, treat the reaction mixture with sodium bicarbonate and extract with ethyl acetate. Concentrate the solution containing the acylated product mixture to a residue, dissolve the residue in methanol and hydrolyze the phenolic acylated hydroxyl moieties using a 20% solution of tetraethylammonium hydroxide in methanol to obtain the title compound.

This example is directed to a general procedure for preparing the N-acylamino compounds of this invention. Other N-acylamino compounds may be prepared by substituting for cyclohexyl carboxylic acid any of the following carboxylic acids: (a) propionic, (b) valeric, (c) dodecanoic (d) pivalic, (e) isopropylacetic, (f) adamantanecarboxylic, (g) cyclobutylcarboxylic, (h) cycloheptylcarboxylic, (i) benzoic, (j) phenylacetic, and (k) γ-phenylbutyric acid to provide the corresponding N-acylamino derivatives of antibiotic 13-384, component 5.

EXAMPLE VI

N-Phenylglycylamino Derivative Of Antibiotic 13-384, Component 5

To a solution of 600 mg of N-carbobenzyloxyphenylglycine in anhydrous methylene chloride add 220 mg of triethylamine followed by 250 mg of ethyl chloroformate while stirring at −20° C. Stir the reaction mixture for ½ hour and add thereto 250 mg of antibiotic 13-384, component 5 and raise the temperature to 25° C. Monitor the reaction by TLC by the procedure described in Example IV. When reaction is complete, add ethyl acetate and wash the resulting organic layer with aqueous sodium bicarbonate solution and concentrate the ethyl acetate layer to a residue. Dissolve the residue in ethanol and hydrogenate at 30 psi, in the presence of palladium for about 20 hours to remove the N-carbobenzyloxy protecting group. Remove the catalyst by filtration, basify the filtrate with 20% tetraethylammonium hydroxide to hydrolyze the phenolic acylated hydroxyl moieties. Concentrate the filtrate to a residue to obtain the title product.

In a like manner, by replacing N-carbobenzyloxyphenylglycine with an equivalent quantity of other α-aminoacids bearing reductively removable amino protecting groups and by following the procedure of this example, the corresponding α-aminoalkanoyl amino derivatives of antibiotic 13-384, component 5 may be produced.

EXAMPLE VII

N-Acetyl-N-Hydroxyl Derivative Of Antibiotic 13-384 Component 1

Treat a solution of 200 mg of antibiotic 13-384, component 1 and 0.2 mL of acetic anhydride in 5 mL of anhydrous THF with 300 mg of activated zinc dust (added in portions) at room temperature for 4 hours. Add 1 mL of conc. aqueous ammonia and stir the mixture for ½ hour. Adjust the pH of the reaction mixture to 6.5 with tartaric acid and extract the aqueous solution with ethyl acetate. Dry the organic layer. Remove the solvent and subject the residue to silica gel column chromatography to obtain the title compound.

Antibacterial properties of the compounds of this invention were determined by both in-vitro and invivo tests against a variety of gram-positive and gram-negative organisms. In-vitro antibacterial activity tests were performed via conventional agar dilution methods in Mueller-Hinton agar (MHA).

What is claimed is:

1. A compound represented by formula I

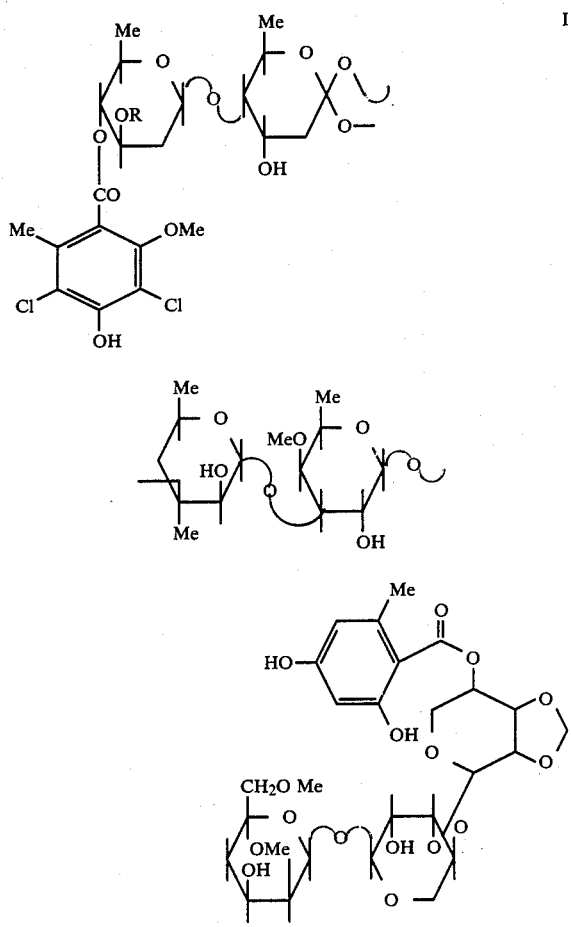

wherein R is hydrogen, or

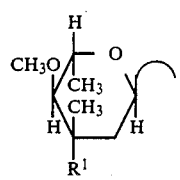

wherein $R_1$ is N-acylamino, N-alkylamino, N,N-dialkylamino, N-acyl-N-hydroxylamino or a pharmaceutically acceptable salt thereof.

2. A compound as defined in claim 1, wherein $R_1$ is N-acylamino.

3. A compound as defined in claim 1, wherein $R_1$ is N-alkylamino.

4. A compound as defined in claim 1, wherein $R_1$ is N,N-dialkylamino.

5. A compound as defined in claim 1, wherein $R_1$ is N-acyl-N-hydroxylamino.

6. An antibacterial composition comprising a compound as defined in claim 1 in an amount sufficient to elicit antibacterial activity against susceptible gram-positive and gram-negative bacteria, together with a pharmaceutically acceptable carrier.

7. A method of eliciting an antibacterial effect in a warm-blooded animal having a susceptible gram-positive or gram-negative bacterial infection which comprises administering to said animal an anti-bacterially effective amount of a compound represented by the formula

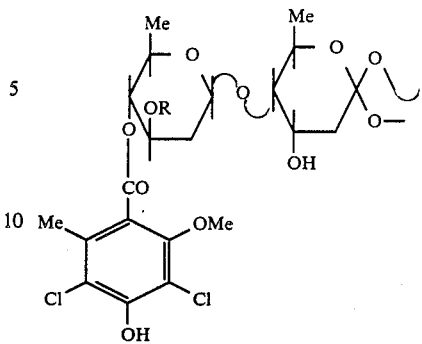

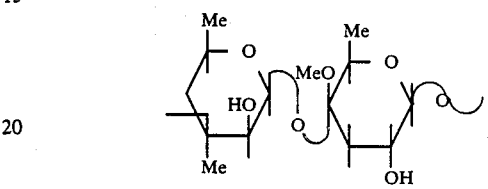

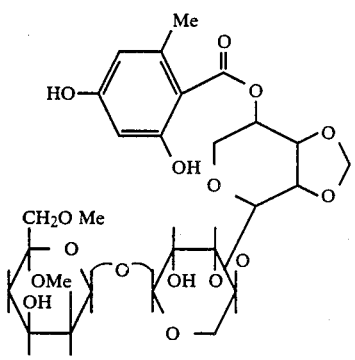

wherein R is hydrogen, or

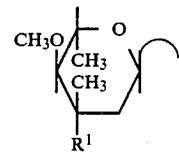

wherein $R_1$ is N-acylamino, N-alkylamino, N,N-dialkylamino or N-acyl-N-hydroxylamino or the pharmaceutically acceptable salts thereof.

8. A method of claim 7, wherein $R_1$ is N-acylamino.
9. A method of claim 7, wherein $R_1$ is N-alkylamino.
10. A method of claim 7, wherein $R_1$ is N,N-dialkylamino.
11. A method of claim 7, wherein $R_1$ is N-acyl-N-hydroxylamino.

* * * * *